United States Patent [19]

Steblay

[11] Patent Number: 4,601,207

[45] Date of Patent: Jul. 22, 1986

[54] MEASURING MINE ROOF BOLT STRAINS

[75] Inventor: Bernard J. Steblay, Lakewood, Colo.

[73] Assignee: The United States of America as represented by the Secretary of the Interior, Washington, D.C.

[21] Appl. No.: 690,810

[22] Filed: Jan. 11, 1985

[51] Int. Cl.$^4$ .................................. G01N 29/00
[52] U.S. Cl. .................................. 73/597; 73/761; 405/259
[58] Field of Search ............ 73/597, 581, 1 DV, 761; 411/8, 14; 405/259, 260, 261

[56] References Cited

U.S. PATENT DOCUMENTS

| | | | |
|---|---|---|---|
| 2,947,279 | 8/1960 | Hohos et al. | 405/259 |
| 3,810,385 | 5/1974 | McFaul et al. | 73/581 |
| 4,062,227 | 12/1977 | Heyman | 73/630 |
| 4,363,242 | 12/1982 | Heyman | 73/579 |
| 4,402,222 | 9/1983 | Olson et al. | 73/579 |
| 4,413,518 | 11/1983 | Jones | 73/597 |
| 4,445,360 | 5/1984 | Treder, Jr. | 73/1 DV |
| 4,471,657 | 9/1984 | Voris et al. | 73/597 |

Primary Examiner—Stephen A. Kreitman
Attorney, Agent, or Firm—Thomas Zack

[57] ABSTRACT

A mine roof bolt and a method of measuring the strain in mine roof bolts of this type are disclosed. According to the method, a flat portion on the head of the mine roof bolt is first machined. Next, a hole is drilled radially through the bolt at a predetermined distance from the bolt head. After installation of the mine roof bolt and loading, the strain of the mine roof bolt is measured by generating an ultrasonic pulse at the flat portion. The time of travel of the ultrasonic pulse reflected from the hole is measured. This time of travel is a function of the distance from the flat portion to the hole and increases as the bolt is loaded. Consequently, the time measurement is correlated to the strain in the bolt. Compensation for various factors affecting the travel time are also provided.

15 Claims, 3 Drawing Figures

MEASURING MINE ROOF BOLT STRAINS

FIELD OF THE INVENTION

The present invention relates generally to the measuring of strain in a mine roof bolt, and more particularly to the ultrasonic measurement of the change of length of a mine roof bolt to determine the strain in the mine roof bolt.

BACKGROUND OF THE INVENTION

Roof falls are the number one cause of coal mine injuries and fatalities. Mine roof bolts are the principal means of roof support to prevent roof falls. Millions of mechanical anchor roof bolts are used each year for this purpose. The benefit of this bolting depends on a number of factors including rock density, bolt length, in situ stresses, time elapsed between mining and installation, rock properties, bolt patterns, and tension.

Installation tension is a major determinant of support quality. Post installation tensions indicate both the usefulness of the individual bolts and the behavior of the reinforced rock structure. The importance of short and long term bolt tension measurements is well recognized and is required by regulations (30 CFR 55, 56 and 57). These regulations also take into account the difficulty of practical tension measurements. Only a statistical sample of the bolts installed are required to be measured using current torque wrench technology. Drawbacks to the torque wrench technology are that the anchorage is disturbed and perhaps weakened, accuracy is limited by friction to about + or −30 percent (+ or −3,500 lbs), and the procedure is relatively time intensive.

Many instrument concepts have been considered in the past for measuring the strain in mine roof bolts. In general, these concepts can be grouped into two categories; those concepts which provide good measurement accuracy but at high cost per bolt, and those concepts which provide low cost per bolt but limited accuracy.

One instrument concept which has been considered in the past is ultrasonic pulse-echo measurement. In this concept, a transducer is mounted on the bolt head to introduce the pulse into the bolt. The time taken to travel down the bolt and reflect back to the transducer is measured. This travel time is obviously related to the bolt length. Once the initial length is determined, the change in travel time is related to a bolt strain. From the geometry of the bolt, or from empirical calibration, this can be related to bolt tension or load.

Although the ultrasonic pulse-echo measurement concept is simple in theory and can be easily applied to the measurement of bolt strain in laboratory situations, the application of such a concept to mine roof bolts is quite complex. Among the complicating factors are the need for extreme time measurement accuracy, the ultrasonically undesirable geometry of mine roof bolts, variations in bolt lengths before installation, variations in effective bolt lengths due to anchor nut positions, stress and temperature effects on ultrasonic velocity, roughly forged bolt constructions including roughly forged heads with raised length and grade markings, the long and narrow geometry of mine roof bolts, plastic strain and signal attenuation caused by bending, portability requirements, gassy mine permissibility requirements, adverse operating environment, and the need for long term repeatability. In contrast, presently available pulse-echo instruments work well only on precision industrial bolts which have flat ends, flat heads, measurable installed effective lengths, tight dimensional tolerances, relatively short lengths, relatively large diameters, relatively mild environments, and no bending.

Various ultrasonic devices have been disclosed in the prior art for determining bolt tension or strain. For example, in U.S. Pat. No. 4,471,657 (Voris et al), an ultrasonic stress measuring method and apparatus is disclosed for measuring the length and stress in a tensile load member such as a bolt. The apparatus includes time interval measuring means for determining the elapsed time between transducer energization and the receipt of a pulse echo. Besides basing the strain on the measured time interval, a variety of other factors are also considered including temperature, tensile load member material, velocity change due to stress forces on the tensile load member material, overall length, elasticity of the tensile load member material, and thermal expansion of the tensile load member material. Other ultrasonic bolt tension measuring devices are disclosed in U.S. Pat. No. 4,062,227 (Heyman) and U.S. Pat. No. 4,402,222 (Olson et al). An ultrasonic device for measuring strain in bolts using a pulse phase lock loop technique is disclosed in U.S. Pat. No. 4,363,242 (Heyman).

Even though there has been a demonstrated need for a low cost, high accuracy method of measuring mine roof bolt strain, such a technique has not been achieved in the prior art.

SUMMARY OF THE INVENTION

In accordance with the present invention, a mine roof bolt and a method of measuring the strain in mine roof bolts are provided. According to the method, a flat portion on the head of the mine roof bolt is first machined. Next, a hole is drilled radially through the bolt at a predetermined distance from the bolt head. After installation of the mine roof bolt and loading, the strain in the mine roof bolt is measured by generating an ultrasonic pulse at the flat portion. The time of travel of the ultrasonic pulse reflected from the hole is measured. The time of travel is a function of the distance from the flat portion to the hole and increases as the bolt is loaded. Consequently, the time measurement is correlated to the strain in the bolt.

In one embodiment of the present invention, a second hole is radially drilled through the bolt at a predetermined distance from the first mentioned hole. The time of travel of the ultrasonic pulse from one hole and back and from the other hole and back is then measured. Thereafter, the travel time between the two holes and hence the distance between these two holes is determined to determine the strain of the bolt.

Preferably, the generating step includes a step of holding the ultrasonic transducer magnetically to the flat portion. In addition, a couplant is preferably positioned between the transducer and flat portion.

Advantageously, the flat portion is initially cleaned to remove any corrosion before the generating of the ultrasonic pulse. To reduce corrosion in the hole, the hole is also preferably filled with a silicon caulking compound prior to installation.

In order to correlate the time measurement to the strain of the bolt, an initial measurement is preferably taken of a sample bolt under known strain conditions. In establishing the correlation, the compensating of the time measurement for change in temperature between the sample bolt and the measured bolt is also preferably made. The strain determination can also be compensated for the error due to possible bending of the bolt. Finally, the time measurement is preferably further compensated by a factor which accounts for the change in propogation velocity of the bolt as the strain increases in the bolt.

It is an object of the present invention to provide a low cost, high accuracy measuring method for measuring the strain in mine roof bolts. The present method is low cost because the bolt preparation requires only simple machining. In addition, no permanently attached instrumentation is required for achieving high accuracy. The accuracies provided should be approximately + or − 50 lbs. in the best circumstances and about + or − 1700 lbs. in the worst circumstances.

It is also an object of the present invention to provide a method using an instrument which can be used to measure the loads in thousands of bolts. By measuring the loads in a large number of bolts, improved safety, improved support design, improved productivity, and improved installation procedures can be achieved.

It is an advantage of the present invention that the method of measurement does not harm the anchorage of the mine roof bolt. It is also an advantage of the present invention that the dynamic behavior of the support structure can be easily monitored using quick and inexpensive measurements of the associated mine roof bolt.

Other features, objects, and advantages of the present invention are stated in or are apparent from the detailed description of a presently preferred embodiment of the invention found hereinbelow.

DETAILED DESCRIPTION OF THE PREFERRED EMBODIMENT

Figure 1:
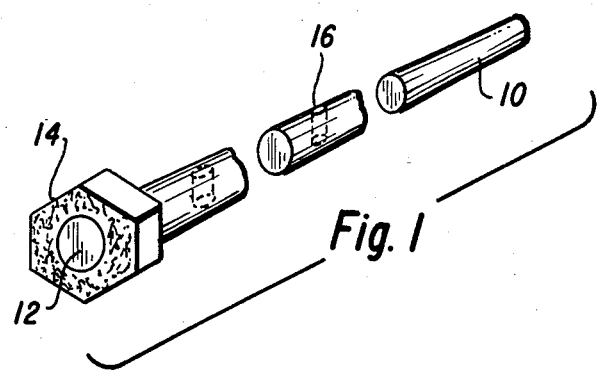
FIG. 1 is, a perspective view of a mine roof bolt machined according to the present invention.

Briefly, the method of the present invention is used to measure the strain or load in a specially adapted mine roof bolt. This measurement is accomplished using an ultrasonic measurement pulse generated by a transducer in contact with the head of the roof bolt. As the heads of mine roof bolts, such as roof bolt 10 depicted in FIG. 1, are usually manufactured quite rough and with grade markings thereon, it is initially necessary to machine a flat portion 12 on the head 14 of roof bolt 10. In addition, since roof bolts are quite long and the ultrasonic pulse quite attenuated during travel therealong, a reflector hole 16 is drilled in roof bolt 10 as shown to reflect back a measurable pulse to the transducer. By measuring the time of travel of the reflected pulse, which increases as the bolt length increases under increasing loads, a correlation is made to the bolt load or strain.

With the method of the present invention, the most important requirement is accurate time measurement of the ultrasonic pulse. The timing must be started at a repeatable point on the output pulse and stopped at a repeatable point on the reflected pulse. These trigger points must stay stable from a no load condition to a failure load condition of the bolt. Measurements using + or − 0.00003 cm (+ or − 0.00001 inch) linear variable distance transducers (LVDT) show that a typical high strength, 1.6 cm ($\frac{5}{8}$ inch) nominal diameter, 1.2 m (4 foot) roof bolt stretches only 0.0015 cm (0.0006 inch) per 444N (100 lbf) load. Considering that the signal makes a round trip, in order to measure a + or −444N (+ or −100 lbf) load accuracy, the time interval must be measured to about $2 \times 10^{-8}$ seconds since the velocity of the signal and bolts is 600,000 cm/sec (232,581 inches/sec). It should be noted that about 72 percent of this time change is due to the stress effect on velocity which is discussed subsequently and that the path length is doubled because the signal makes a round trip through the bolt.

The requirement for extreme accuracy of the timing signal must be appreciated because it relates to all the other factors affecting the measurement. Sources of distortion that would alter the trigger points are temperature change, bending, torsional loading, change in coupling quality, change in position, and slight material and geometrical variations.

Figure 2:
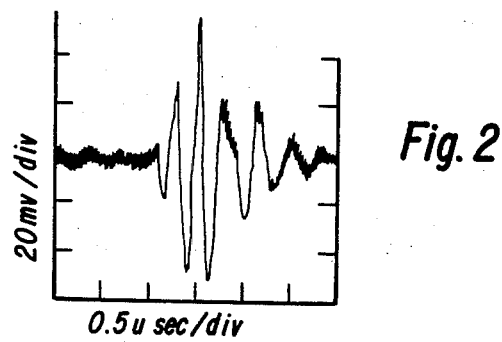
FIG. 2 is a graphical representation of a reflected ultrasonic pulse in the mine roof bolt depicted in FIG. 1.

A typical reflected pulse is depicted in FIG. 2. The only points on the signal which are stable in time as signal amplitude varies are the peaks and zero crossings. Presently, the best commercial units first use a wide range, high quality automatic gain control in combination with a zero crossing detector. The automatic gain control minimizes any amplitude changes in the processed signal and the zero crossing circuit sets the trigger point at the most stable part of the signal. Averaging many pulses also improves accuracy. Instrument resolution is 0.0001 inches. This ensures that instrument error will not govern overall accuracy. This means that a stable, repeatable time interval measurement of + or $-3 \times 10^{-9}$ seconds must be made.

Another important characteristic of any instrument to be used is that it must provide a very high voltage output pulse to the transducer. When bolt end reflection is used, the received signal is about 1/1,000th of the input signal. However, when other reflectors are used such as the holes discussed subsequently, the received signals drop to about 5/10,000th's of the input signal. Thus, the output signal needs to be about 300 volts to provide a usable signal level. Overall power can, however, be quite low since the pulse duration may be only 0.3 microseconds and the repetition about every 4 milliseconds. For gassy mine permissibility, capacitive storage should be less than 3 millijoules and it has been suggested that a more conservative 0.3 millijoules be used.

The reflective signal consists of a number of pulse brackets because the path is longer than the transducers near field focus range. The signal takes a number of paths as waves are reflected off of outside surfaces, mode converted between P and S types, and constructively and destructively combined. For this reason, it is necessary for the instrument used to ignore signals for a selectable amount of time. This thus allows the selection of a particular packet, which is needed to get the most desirable wave shape and the least change in shape in mine installations which almost always involve bending. It is also necessary to suppress undesired reflections which occur from the bolt head and end. According to the present invention, time dependent gain circuitry is used to accomplish this. This circuitry allows suppression of reflections that occur well before or well after the time of the desired reflection which is known in advance.

According to the present method, the instrument used is also properly calibrated to compensate for stress and temperature effects. As mentioned above, increasing tension (stress) lowers velocity. This causes an increase in the measured time interval which is indistinguishable from strain-caused change. However, since this effect is linear, it can be compensated for by using a multiplication factor. For typical mine bolts, this multiplication factor is 0.28. It should be appreciated that a positive side effect of the multiplying of the raw time reading by the multiplication factor is that error sources which alter path length are reduced by 72%.

Temperature caused expansion or contraction also alters actual path length. To compensate properly for temperature, axial changes need to be separated from volumetric changes and temperature caused velocity changes. Contraction along the bolt axis, for example, produces a real increase in bolt strain since the bolt is firmly anchored in rock which has a very low coefficient of thermal expansion. Due to the long narrow geometry of a rock bolt, the signals follow an angular path throughout the volume of the bolt. Similar contractions laterally change path length, but do not change bolt strain since the bolt is free to expand laterally. A 5 degree C. change produces a total path change effect equivalent to a 6,700N (1500 lbf) load change. Using a linear coefficient of expansion of steel of $1.17 \times 10^{-5}$/degree C., the true strain effect can be determined to be about 2,200N (500 lbf). The remaining effect must be compensated for in the instrument calibration. Fortunately, it is linear with respect to temperature and the compensation is accomplished by applying the proper multiplication factor. The temperature must, however, be measured to make this correction. It should also be appreciated that part of the temperature effect is probably due to velocity change as well. For mine roof bolts, the proper temperature calibration is about 0.66 times the factor which would be determined by industry standard calibration.

It should be realized that the present method is designed to be accomplished with an instrument that is easily portable. Overall power drain and voltage levels are also designed to be consistent with MSHA gassy mine permissibility requirements. While no instrument meeting these requirements is presently available, it is possible to modify presently available equipment. For example, a Raymond Bolt Meter manufactured by Raymond Engineering Inc., Power-Dyne Division, of Middletown, Connecticut, PDX 934 Volt Gage was effectively modified for this purpose. The modifications consisted of protective circuitry, redesigned battery charging arrangement, protective packaging, and component value changes were made. In particular, safety resisters were added to the battery terminals and to all power supplies derived from the basic battery voltage. The drive pulse circuitry peak power levels must be reduced as mentioned above. This is accomplished by balancing peak voltage levels with the amount of capacitance used. Typical compromises are 0.05 microfarads and 300 volts. While an explosion-proof reasonably rugged case would be possible, such a case would be heavy and would adversely effect portability.

The selection of a suitable transducer for use with the present invention should be made with regard to the transducers currently available as the state of this art improves. One consideration for the transducer is the bolt head dimension. The bolt head dimension places a restriction on the overall diameter of the transducer which must be less than 1.9 cm (0.75 inches). In addition, to keep the couplant forces relatively consistent, a magnetic hold down is required. With magnetic hold-down, variations in couplant thickness can be held to 0.0005 cm (0.0002 inches) or less if a low velocity couplant is used. Beyond this, the transducer chosen must provide the best balance between the conflicting requirements of high signal amplitude and good damping. If there are numerous approximately equal level peaks in a signal packet, the trigger may jump to different points as slight distortions occur. Therefore, the driving pulse must be rapidly damped. However, signal attenuation is severe particularly if small area reflection targets are used. Consequently, it is desirable to get the maximum possible energy into and out of the bolt. Some standard and special transducers from various manufacturers which meet these requirements to a usable degree are available.

A suitable transducer provides at least 0.35 volt return signal from a 300-volt pulse. This pulse was reflected from a 0.04 inch diameter transverse hole located 15 inches from the bolt head. This 15 inch reflector distance represents a current limit of operation as signals attenuate rapidly with distance and smear out. In such a situation, instead of one prominent peak, a train of peaks is produced. This makes peak jumping more likely, particularly as bending distorts the waves. However, it should be appreciated that many error sources are constant with respect to bolt load such as those caused by variations in couplant thickness or bolt to bolt reflector hole position variation. This makes it desirable to make the reflector distance as large as possible so that these errors are a small percentage of the signal path length. However, signal attenuation also makes it desirable to shorten the reflected distance. The 15 inch distance chosen has been found to be the best compromise between these conflicting requirements.

It should be appreciated that the use of magnetic hold-down for the transducer provides a most consistent reinstallation repeatability. As the present invention is designed to measure a large number of bolts, each reinstallation of the transducer should be as nearly identical to the previous one as possible. The use of a suitable couplant such as glycerine on the transducer also insures good signal transmission for each bolt. A transducer-holding fixture shaped to match the square bolt head is also preferable to help insure proper reorientation of the transducer for each bolt measured. The fixture could also hold a spring loaded thermocouple to measure bolt temperature as necessary for the reasons discussed above.

A potential problem that is solved by the transducer is the introduction of an undesirable wide-band signals into the bolt by the driving pulse. The driving pulse is preferably an extremely fast rise narrow pulse containing many frequency components. The concern is that since each frequency travels at a somewhat different velocity; distortion will occur and cause timing errors. However, transducers act as extremely efficient filters centered at their resonance frequencies. Thus, this potential problem does not occur because the transducer limits the driving pulse to a very narrow frequency band.

As mentioned above, transducer couplant material is necessary and is also a consideration in overall system accuracy. High velocity shear wave couplants allow coupling to a rougher surface but increase couplant thickness variability problems and thus reduce repeatability. With the use of glycerine as a couplant, it has been found that glycerine fills small surface voids, provides good signal strength, and provides a repeatable layer thickness. Overall repeatability using glycerine on a 1.2 m (4 inch) mine bolt with a 38 cm (15 inch) reflector distance was about + or − 0.00025 cm (+ or − 0.0001 inch). This equates to a + or − 222N (+ or − 50 lbf) load.

In addition to good signal strength combined with good damping, the transducer should also produce a wave that is minimally affected by bolt bending. Selecting the optimum center frequency is one aspect of this problem. 2.25 MHz is the best common available frequency which has been found. A complex combination of transducer mass, conversion efficiency, and other factors influence the signal quality. Some signal packets are unusable because gross distortions occur which would cause peak jumping.

It should also be appreciated that the nature of the mine roof bolt themselves produce many measurement problems. For example, the bolt heads are dimpled and stamped with grade and length marks. Since the transducers must be coupled to a flat surface, special preparation techniques are used according to the present invention. While it would be possible to lathe turn flat the entire head, it has been found that this sometimes leaves too short of a head for the bolting machine to grip and install. For this reason, according to the method of the present invention, only the center portion of the bolt head is prepared to receive the transducer head.

It should be appreciated that mine roof bolts are relatively roughly forged and rolled. Length variations for a 1.2 m (4 foot) nominal bolt are on the order of 0.16 cm (0.062 inches) even within the same lot and vary as much as 1 cm (0.4 inch) between manufactures. Since variations of a few ten thousands of an inch need to be measured, the use of end reflections would be impossible unless each bolt were individually calibrated. Such individual calibration would clearly be unsatisfactory for a wide spread mine use. To overcome this limitation, the present invention makes use of a 0.04 inch diameter hole drilled transversely through the bolt to serve as a uniform reflector. If the bolt head to hole distance is kept to + or − 0.0025 cm (+ or − 0.001 inch) and a 38 cm (15 inch) distance to the hole is used, the uncertainty in the bolt load from this source would be + or − 1,332N (+ or − 300 lbf).

An initial concern with the technique for providing a hole as a reflector is that it might weaken the bolt. However, tests were conducted on about 30 drilled and undrilled high strength and extra high strength 1.6 cm (⅝ inch) nominal diameter bolts. These tests showed no discernable effects on yield strength or ultimate strength because of the presence of reflector holes. Although the high strength bolts did often break at the hole, the loads at which the break occurred were the same as with undrilled bolts.

The use of holes as a reflector also solves a second problem with bolts of this type. With the present invention, the instrument directly measures only total strain in the bolt. To calculate tension, the length of the bolt under strain (effective length) must be known so that normalized strain can be determined. The effective length of the bolt varies because the set position of the expansion anchor nut on the thread varies. These variations would cause a substantial error if the bolt end were used as a reflector. With the hole used as a reflector, however, a uniform gage length is established for all bolts. Thus, calibration for one bolt is valid for all bolts of the same type.

It should also be emphasized that the stress in bolts is not uniform. Bolt tension generally refers to the relatively uniform stress in a constant cross section, main body of the bolt. Stress is different due to different cross sections in the tapered zone near the head, in the threads, and in the transition zones in the head and the nut. Stress is obviously highest at the smallest diameter at the root of the threads. However, tests have shown that bolts rarely fail at the threads despite the highest stress at this point. The lack of failure at the threads is presumably due to the strength increases through work hardening from the thread rolling or stamping process.

Another problem affecting measurement with mine bolts is bending. Bending occurs even in a horizontal mine area due to misalignment of the drill and the mine roof. Forces produced by bending are quite great. Bending of only a few degrees will produce plastic deformation. Bending weakens the overall signal because of the curved path and distorts the signal packets due to changed reflection points. This makes it difficult to stay triggered on a particular peak. It also produces a permanent change in path length which will be read by the instrument as if it were a portion of the elastic strain. If the instrument used can remain locked to the proper peak, in spite of the distortions, a severe bend of 10 degrees produces an instrument offset of about + or − 0.0064 cm (+ or − 0.0025 inch) with a 38 cm (15 inch) reflector distance. This would be equivalent to a load error of + or − 5,782N (+ or − 1,300 lbf).

Figure 3:
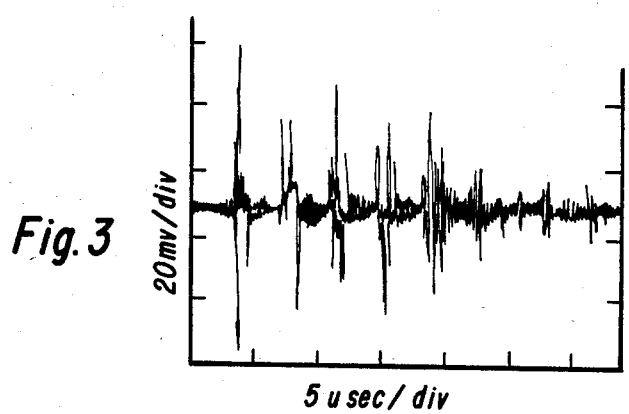
FIG. 3 is a graphical representation of the spacing of various signal packets produced by various travel paths of an ultrasonic pulse in a bolt.

Staying locked to the proper peak at a reflector distance such as proposed pushes the state of the art of the instrument and transducer technology to its limits. The automatic gain control circuitry must then be capable of compensating for most of the signal loss caused by the bending. The transducer must produce and convert as much of the signal as possible. The spacing of the signal packets which represent various travel paths in the bolt are shown in FIG. 3. The spacing allows selection of the packet least effected by bending if the instrument has the ability to ignore trigger levels that occur before an adjustable delay time (blanking adjustment). As shown, the packet spacing is about 2 microseconds regardless of the frequency of the transducer being used. Since the change in travel time from a bolt with no load to a yielded bolt is about 1 microsecond for a 38 cm (15 inch) reflector distance, no interference or packet skipping occurs. Use of this selection technique is critical for a bolt subject to bending because some packets will distort badly causing loss of trigger point and a failed measurement. Experimentation has shown that the second and fourth packets are less affected by bending than the others. While it would be desirable to use the same technique to select a peak within a packet, this is not possible because the peak spacing is only about 0.3 microseconds.

Of course, the best way to handle bending problems is to eliminate them. A roof preparation device has been devised at the Bureau of Mines which eliminates this bending problem. The device consists of a disk on which a weldable abrasive such as cut-rite has been placed. The disk is then fastened to the final piece of drill steel. As the bolting machine finishes drilling the bolt hole, a flat surface is created on the roof perpendicular to the hole. The head plate of the bolt then lies against this flat, perpendicular surface and no major bending occurs. This technique would be recommended whenever it can be applied in conjunction with the present invention. Preserving maximum bolt strength is a peripheral benefit of using this technique as well.

Since the bending which occurs generally occurs near the bolt head and produces a fixed offset error, increasing the signal path minimizes the percentage of measurement error. With a bolt length of 38 cm (15 inch), the error of about + or − 5,782N + or − 1,300 lbf) load caused by bending represents only a 13 percent measurement error in a high strength bolt installed at 80 percent of yield load. This compares favorably with a typical torque wrench accuracy of about 30 percent under the same conditions. As improvements in transducer technology occur, increased reflector distance would reduce this bending error even further.

An alternative technique according to the present invention for eliminating bending errors is to use two or more reflector holes and measure the length change between these holes. By locating the holes beyond the near head section, where the bending occurs, the bending offset is cancelled out.

A related source of potential problems to bending is torsional loading. Since bolts are loaded by turning the head, there is a potential for signal distortion as the bolt shaft and reflector hole are twisted. However, with the high quality of the automatic gain control circuitry used and the selection of an efficient transducer, no significant reduction in accuracy over straight axial loading was found.

It should be appreciated that it is of vital importance to the present invention to repeatedly drill the holes at repeatable distances in the bolt. It has been found that a drill operated at about 8,000 rpm produces a consistently cut hole suitable for use with the present invention.

The flat portion produced on the head of the bolt must also be carefully produced. A two stage grinding process to produce a ¾ inch diameter flat on the bolt head using a fixture to hold the bolt has been found to be satisfactory. A center cutting, flat, carbide, ¾ inch diameter end mill with a ¼ inch shaft is used to create the flat. The end mill is turned by a ¼ inch drill motor. Subsequently, a similar ¼ inch diameter mill is used to eliminate any center high spot. The ¾ inch diameter flat leaves the full outside head length intact so that the bolt installation machine can still properly grip the bolt. The flat portion then allows good coupling to a ¾ diameter transducer as mentioned above.

Accelerated corrosion tests using crushed salt-potash ore in a moist chamber have shown that a typical layer of bolt head corrosion produces an error of + or − 1,334N (+ or − 300 lbf) load in the instrument reading. This occurs because the instrument assumes any change in path length, including the thickness of a corrosion oxide layer, is due to tension change. In ordinary mine environments, it is anticipated that this error would be low enough that it would not be of major significance. However, in environments where substantial corrosion deposits might occur, this problem could be substantially eliminated by using commercial couplant material especially formulated to protect against corrosion and by wire brushing the surface before making a measurement.

It should also be appreciated that a potential for bolt weakening occurs if corrosion is allowed to develop at the reflector hole. For this reason, it is recommended that the reflector hole be filled with one of the commonly available, room temperature setting, silicon caulking compounds or sealants before installation.

The instrument used with the present invention is preferably calibrated by pulling sample bolts in a universal testing machine and comparing the load readings to the instrument readings. The resolution of the universal testing machine used was 50 lbf. While it is possible that the ultrasonic instrument used with the present invention could detect smaller load changes than this, this is more than satisfactory for the application desired.

It is contemplated that for general mine use purposes, it would be satisfactory to calibrate a few samples of a given grade bolt from a given manufacturer. Subsequently, if a manufacturing change is implemented or a different manufacturer or steel supplier is selected, it would be wise to recheck the calibration. As long as the bolts are manufactured to ASTM specifications, no significant variations in calibration would be expected, however.

The principal calibration discussed above can also be supplemented with other calibrations as needed. For example, bolts can be instrumented with strain gauges. A group of three or four gauges around the bolt surface could also be used as an average to minimize bending effects. Bridge configurations can also be used to minimize temperature effects. Strain gauges provide a calibration equal to or better than the resolution of the ultrasonic instruments.

Because the quantity being directly measured by the instrument is strain, accurate linear variable distance transducers (LVDT) were used to provide a direct calibration during experiments. One LVDT calibrated to + or − 0.0001 cm (+ or − 0.00005 inches) was placed at each end of a bolt. The bolt was then loaded through a heavy wall sleeve arrangement. This provided an accurate calibration of actual bolt stretch versus instrument reading and allowed accurate setting of the stress factor and velocity calibration switches on the instrument. It should be noted that the instrument would properly read accurate bolt strains even with these settings roughed in. To measure actual bolt length, however, these settings need to be accurate. If this calibration is performed, there is a spinoff application of determining actual length of installed bolts whose lengths are unknown.

It should also be appreciated that it is necessary to calibrate the instrument for bolts which are loaded torsionally, as the bolts in a mine are. To do this, the load on a bolt was measured using a quartz load cell insensitive to torsion. This calibration is necessary to show that the mechanical distortion of the hole caused by torquing the bolt would not adversely affect instrument accuracy. Experiments of this type also showed the relaxation or bleedoff experienced in mine bolts after installation.

The velocity calibration can be further refined by using stub sections of bolts cut to known lengths. By holding temperature constant and changing the velocity switch settings until an accurate length reading is obtained on several different lengths stubs, a very accurate calibration is obtained.

The highest accuracy with the present invention can be achieved on unbent bolts that have been individually calibrated. In such a situation, the limiting error is the ability to repeat the transducer position and couplant thickness as measurements are repeated. Experiments have shown that a typical accuracy of + or − 220N (+ or − 50 lbf) load equivalent can be achieved. This technique, however, would be suitable primarily for high accuracy research studies and not for routine mine use.

The measurement of this type has been shown to be relatively insensitive to transducer orientation, though it is best to orient the transducer approximately the same each time.

Where a sample bolt representing an entire lot is calibrated and the calibration is assumed to hold for all of the rest of the bolts, the limiting error, assuming the bolt is unbelt, is the repeatability of locating and shaping the reflector hole. Because changes in travel time caused by hole position are multiplied by the stress correction factor (0.280), the position and shape errors are reduced by this amount. An error of + or − 0.0025 cm (+ or − 0.001 inch) in position which translates into a path length error of 0.0051 cm (0.002 inch), causes an equivalent error of + or − 1,334N (+ or − 300 lbf) load using a 38 cm (15 inch) reflector distance. Combining this source of error with the relocating error which is also present, the overall accuracy of the present invention would be about + or − 1,779N (+ or − 400 lbf) load.

As mentioned above, severe bending causes the greatest reduction of accuracy. Because bending produces a real offset in path length, the instrument measures this offset as if it were a load induced strain. The stretch measured by the instrument is about 0.013 cm (0.0050 inches) with a 10 degree bend, which is consistent with the expected offset due to plastic deformation. Since the offset is always measured as an increase in length, the instrument calibration can be set for half the expected error. This makes the error + or − 0.0064 cm (+ or − 0.0025 inches) or + or − 5,782N (+ or − 1,300 lbf) load equivalent. Adding in the other error sources, total accuracy if a bent mine roof bolt is being measured is about + or − 7,562N (+ or − 1,700 lbf) load. This reading seems to be insensitive to the relative orientation of the reflector hole to the bend.

Corrosion also produces a path length change which is again multiplied by the stress correction factor. Accelerated corrosion tests show typical error equivalents of + or − 1,334N (+ or − 300 lbf) load as mentioned above. Cleaning procedures and the use of a corrosion inhibiting couplant helps to minimize this error source. However, if the bolt measured shows corrosion on the head measuring surface, this error could be added to the other error sources. In such a situation, the calibration could be offset to compensate for the always increased path length caused by corrosion as well to minimize the error effect.

Although the present invention has been described with the use of an instrument employing a pulse-echo technique, it should be appreciated that other techniques can be used to measure elongation of the bolt. For example, the time measurement of the ultrasonic pulse can be indirectly measured using a phase difference technique. This technique has a potential resolution greater than direct measurements. However, presently available instruments using this technique do not adequately compensate for amplitude variations discussed previously and have other drawbacks for the mine roof bolt application. This type of technique is disclosed in U.S. Pat. No. 4,363,242 (Heyman) discussed above. It should be noted that the device disclosed in this patent is not usable in a gassy mine environment, but the technique disclosed is suitable for the type of measurement required and a suitable device could possibly be adapted for use in a gassy mine environment.

The primary use of the measurement process of the present invention is to measure the absolute load history of prepared bolts for purposes of safety, production, research, and regulation compliance. The process makes it easy and inexpensive to take frequent load measurements. This allows monitoring of structural behavior on a dynamic basis.

A second application would be to measure the length of unprepared bolts. Since the grinding apparatus is highly portable and can be used with a battery-powered drill motor, the head of an already installed bolt can be readily prepared for transducer coupling. The length of an unknown mechanical or resin bolt can then be determined to about + or − 0.1 inches.

A third application would be to measure load change of an unprepared mechanical or resin bolt already installed. The same head preparation technique is used. Absolute load can be determined only to an accuracy dependent on the accuracy to which the no-load effective length can be estimated. Load change from the time of the initial measurement can be determined with high accuracy, however.

Thus, while the present invention has been described with respect to an exemplary embodiment thereof, it will be understood by those of ordinary skill in the art that variations and modifications can be effected within the scope and spirit of the invention.

I claim:

1. A method of measuring the strain in mine roof bolts comprising the steps of:
   machining a flat portion on the head of the bolt before loading;
   drilling a reflector hole radially through the diameter of the bolt at a predetermined distance from the bolt head before loading, the ratio of the diameter of the hole to the diameter of the bolt being less than 0.10 to prevent weakening of the loaded bolt;
   generating an ultrasonic pulse at the flat portion after loading;
   measuring the time of travel of the ultrasonic pulse reflected from the hole, which increases as the bolt is loaded; and
   correlating the time measurement of the strain in the bolt.

2. A method of measuring strain as claimed in claim 1 wherein the generating step includes the step of holding an ultrasonic transducer magnetically to the flat portion.

3. A method of measuring strain as claimed in claim 2 wherein the generating step includes the positioning of a couplant to the transducer.

4. A method of measuring strain as claimed in claim 3 and further including the step of initially cleaning the flat portion of corrosion before generating the ultrasonic pulse.

5. A method of measuring strain as claimed in claim 2 wherein the generating step includes the generating of about a 2.25 MHz pulse.

6. A method of measuring strain as claimed in claim 1 wherein the drilling step includes the locating of the hole approximately 15 inches from the bolt head.

7. A method of measuring strain as claimed in claim 1 wherein the correlating step includes the initial measuring of time measurements of a sample bolt under known strains to determine the correlation between time measurement and strain.

8. A method of measuring strain as claimed in claim 7 wherein the correlating step also includes the compensating of the time measurement for changes in temperature between the sample bolt and the measured bolt.

9. A method of measuring strain as claimed in claim 8 wherein the correlating step also includes the compensating of the time measurement for one-half of the expected error due to possible bending of the bolt.

10. A method of measuring strain as claimed in claim 8 wherein the correlating step also includes the compensating of the time measurement by a factor which accounts for the change in propagation velocity of the bolt as strain increases.

11. A mine roof bolt which is adapted for measuring the strain therein using an ultrasonic pulse measurement technique comprising:
a bolt head including a flat end portion, said flat portion being adapted to receive an appropriately sized ultrasonic transducer; and
a reflector radial hole through the diameter of the bolt at a precise predetermined distance from said flat portion to act as a pulse reflector, the ratio of the diameter of the radial hole to the diameter of the bolt being less than 0.10 to prevent weakening of the loaded bolt.

12. A method of measuring the strain in mine roof bolts comprising the steps of:
machining a flat portion on the head of the bolt before loading;
drilling a hole radially through the bolt at a predetermined distance from the bolt head before loading;
generating an ultrasonic pulse at the flat portion after loading;
measuring the time of travel of the ultrasonic pulse reflected from the hole, which increases as the bolt is loaded;
correlating the time measurement to the strain in the bolt;
machining a second hole radially through the bolt at a predetermined distance from the first-mentioned hole;
measuring the time of travel of the ultrasonic pulse from one hole and back and from the other hole and back; and
determining the travel time and hence distance between the holes.

13. A method of measuring the strain in mine roof bolts comprising the steps of:
machining a flat portion on the head of the bolt before loading;
drilling a hole radially through the bolt at a predetermined distance from the bolt head before loading;
generating an ultrasonic pulse at the flat portion after loading;
measuring the time of travel of the ultrasonic pulse reflected from the hole, which increases as the bolt is loaded;
correlating the time measurement to the strain in the bolt; and
filling the hole with a silicone caulking compound.

14. A mine roof bolt which is adapted for measuring the strain therein using an ultrasonic pulse measurement technique comprising:
a bolt head including a flat end portion, said flat portion receiving an appropriately sized ultrasonic transducer;
a radial hole in the bolt at a precise predetermined distance from said flat portion which acts as a pulse reflector; and
a silicone sealant located in said hole to prevent corrosion of said hole.

15. A mine roof bolt which is adapted for measuring the strain therein using an ultrasonic pulse measurement technique comprising:
a bolt head including a flat end portion, said flat portion receiving an appropriately sized ultrasonic transducer;
a radial hole in the bolt at a precise predetermined distance from said flat portion which acts as a pulse reflector; and
a second radial hole in the bolt at a precise distance from said first-mentioned hole, said second hole also acting as a pulse reflector.

* * * * *